United States Patent [19]

Metzner

[11] Patent Number: 5,669,278
[45] Date of Patent: Sep. 23, 1997

[54] KNIFE HOLDER FOR RECEIVING A WEDGE-SHAPED MICROTOME KNIFE

[75] Inventor: Rolf Metzner, Dossenheim, Germany

[73] Assignee: Leica Instruments GmbH, Wetzler, Germany

[21] Appl. No.: 608,534

[22] Filed: Feb. 28, 1996

[30] Foreign Application Priority Data

Feb. 28, 1995 [DE] Germany ............ 195 06 837.8

[51] Int. Cl.⁶ .................................................. G01N 1/06
[52] U.S. Cl. ............... 83/165; 83/698.31; 83/699.61; 83/915.5
[58] Field of Search .................. 83/699.61, 698.31, 83/699.51, 856, 915.5, 703, 707, 713, 162, 165

[56] References Cited

U.S. PATENT DOCUMENTS

| | | | |
|---|---|---|---|
| 2,662,445 | 12/1953 | Jacoby, Jr. | 83/699.61 |
| 3,203,290 | 8/1965 | Ashby | 83/915.5 X |
| 3,227,020 | 1/1966 | Zeytoonian | 83/915.5 X |
| 4,207,790 | 6/1980 | Endo |  |
| 4,472,989 | 9/1984 | Endo | 83/699.61 X |
| 4,690,023 | 9/1987 | Berleth et al. |  |
| 4,700,600 | 10/1987 | Pickett | 83/915.5 X |
| 5,099,735 | 3/1992 | Kempe et al. | 83/699.61 |

FOREIGN PATENT DOCUMENTS

| | | |
|---|---|---|
| 1 962 695 | 6/1967 | Germany . |
| 21 40 796 | 2/1973 | Germany . |
| 21 43 529 | 3/1973 | Germany . |
| 28 52 373 | 3/1979 | Germany . |
| 34 13 251 | 2/1985 | Germany . |

*Primary Examiner*—Eugenia Jones
*Attorney, Agent, or Firm*—Foley & Lardner

[57] ABSTRACT

A knife holder for receiving wedge-shaped microtome knives, in particular regrindable hard metal or steel knives, has a base and upwardly open right and left clamping jaws for receiving the knife. The upwardly open configuration allows easier exchange of knives. The clamping jaws are mounted pivotably to the base to allow clearance angle adjustment of the cutting knife. Each clamping jaw has a clamping screw for securing the cutting knife in the clamping jaws. A height-adjustable knife rest is provided for supporting the back of the knife. A clamping plate is detachably positioned between the knife and the clamping screws, which clamping plate bridges the distance between the clamping jaws for stabilizing the cutting knife. The holder has at least one spring suspension for suspending the clamping plate to the clamping jaws. In the region between the two clamping jaws, the clamping plate has a tapering shaped lead-off section contiguous with the knife to form a virtually projection free plane so that the cut samples can slide off evenly.

20 Claims, 3 Drawing Sheets

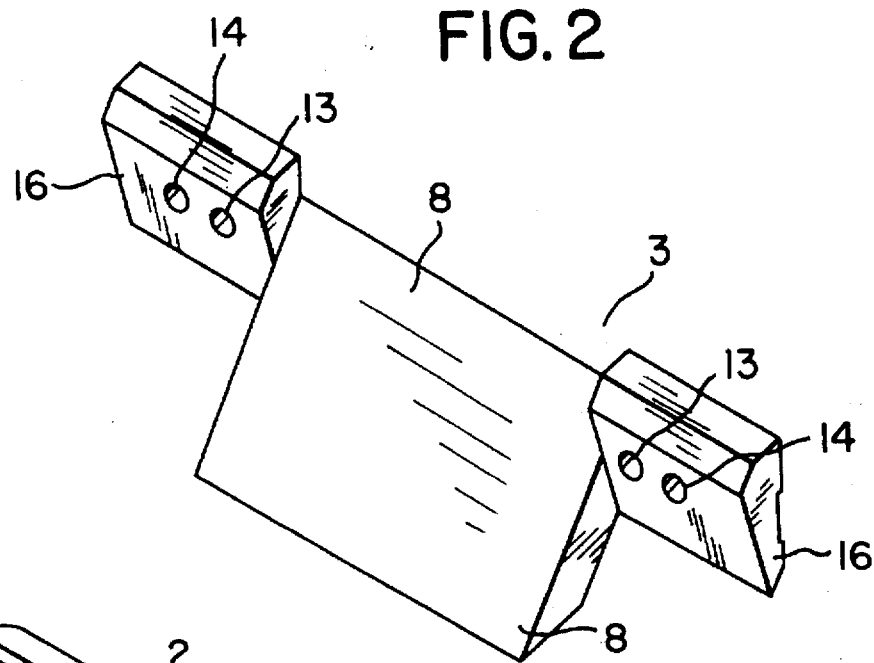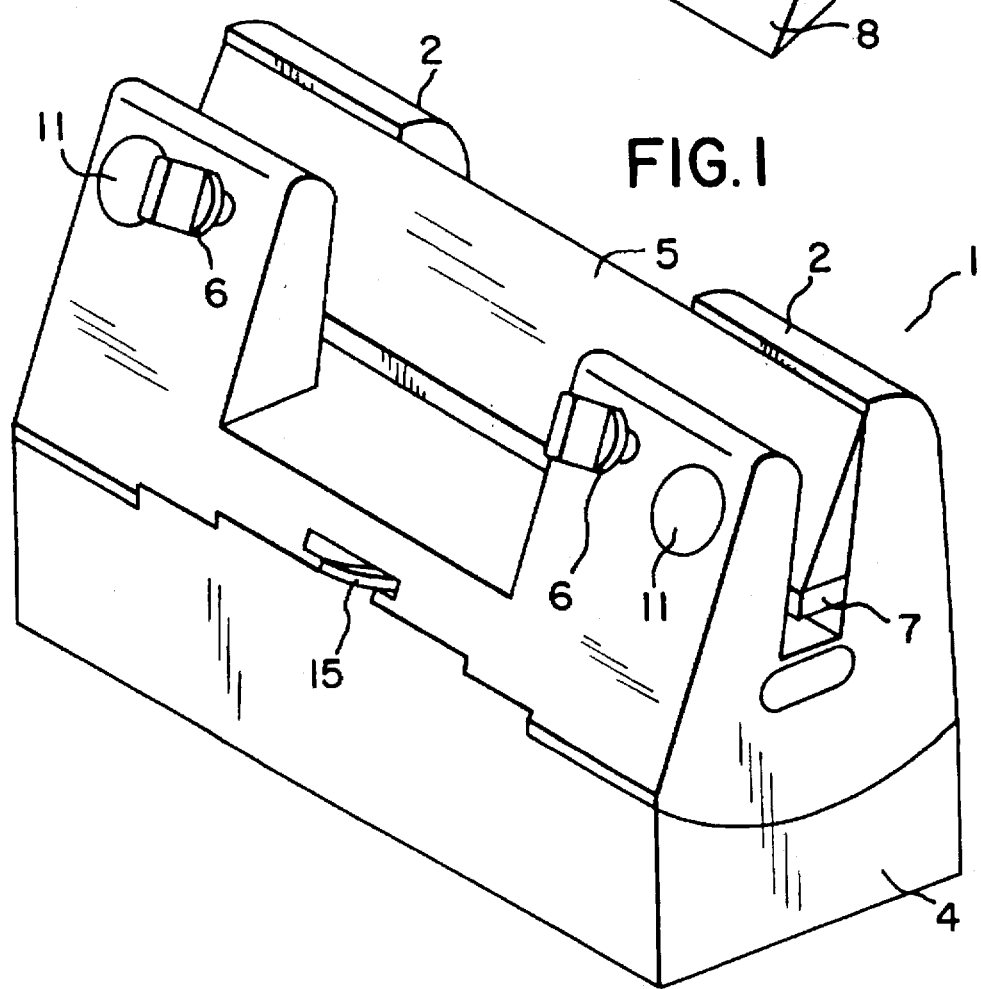

KNIFE HOLDER FOR RECEIVING A WEDGE-SHAPED MICROTOME KNIFE

BACKGROUND OF THE INVENTION

Wedge-shaped cutting knives made of hard metal or from steel are used over a relatively long period and, in contrast to simple disposable blades, can be reground. These wedge-shaped cutting knives are, as a result of their geometry, very stable so that they can be used in a simply constructed knife holding device. To this end, knife holders that have right and left clamping jaws are known. The clamping jaws are designed in an upwardly closed manner so that the cutting knife has to be inserted into these clamping jaws. The fixing of the knife takes place via screws, which act on the rear surface of the knife.

For alignment of the cutting knife on the object to be cut, the knife holder is usually mounted pivotably on a base and also has a height adjustment system for the knife in order to compensate for different geometries caused by knife regrinding. Such a knife holder is illustrated and described for example in DE 21 43 529.

A disadvantage of these known knife holders is that the two clamping jaws are designed in an upwardly closed manner for reasons of stability and consequently the cutting knife can be inserted only laboriously into the corresponding guide.

In practice, it has also emerged that, in spite of the stable knife shape, the cutting knife must be fixed additionally in the blade region in certain applications. Such a knife holder is described in DE 34 13 251. The multi-part knife holder has in this case a continuous abutment arrangement in addition to two closed supports. The cutting knife is supported with one of the knife rear surfaces on this abutment arrangement. The gripping of the cutting knife takes place via a continuous clamping jaw, which is actuated via an eccentric shaft and acts on the other knife rear surface.

Very high stability is achieved in the blade region of the knife with this knife holder. However, it has to be accepted in this connection that the cut samples are pushed onto the clamping jaw and as a result can be removed only with difficulty. For these reasons, both knife holders are used in practice according to application. This has the consequence, however, that a changing over of the microtome can take place only by an exchange of the entire knife holder.

From the publications DE 28 52 373 A1, DT 21 40 796 B2 and DE-GM 1 962 695, knife holders for receiving thin knives, the so-called disposable blades, are known. In contrast to the wedge-shaped, regrindable knives made of steel or hard metal, these disposable blades have an unstable construction. They are therefore clamped in firmly by these special knife holders over their entire length between two gripping plates. For safe section lead-off, the clamping jaw tapers in this case in a wedge-shaped manner in the blade region. The use of such knife holders is, however, limited to disposable blades.

It is therefore the aim of the present invention to improve a simply constructed knife holder, such as is described in DE 21 43 529, for example, in such a manner that it can, with simple means, be changed over to a knife holder with increased stability in the knife blade region. This aim is achieved according to the present invention by the features described below.

SUMMARY OF THE INVENTION

The present invention relates to a knife holder for receiving a wedge-shaped knife, in particular a microtome knife formed of regrindable hard metal or steel. According to the present invention, the knife holder comprises a base and right and left clamping jaws for receiving the knife therebetween. The clamping jaws are upwardly open to allow easier exchange of knives. Preferably, the clamping jaws are integrally formed as a single piece and pivotally attached to the base to allow a clearance angle adjustment for the knife. Each clamping jaw has a clamping screw for securing the cutting knife in the clamping jaws. A height-adjustable knife rest is included to support the knife, in particular, the back of the knife opposite the cutting edge. The present invention utilizes a clamping plate, preferably of a single, integral piece design, suspended between the knife and the clamping screws to stabilize the cutting knife against the clamping jaws. Further, the knife holder has at least one spring suspension for securing the clamping plate to the clamping jaws. Preferably, two spring suspensions suspend the clamping plate and leave a gap between the clamping jaws and the clamping plate to allow unhindered insertion of the cutting knife.

Each clamping screw has a conical tip that abuts against the clamping plate. Specifically, the clamping plate has a pair of holes for receiving one of the conical tips. The clamping screws are threaded to the clamping jaws so that they can move toward and away from the clamping plate. The axes of the holes or the holes are vertically offset slightly higher in relation to the clamping screw tips to force the clamping plate downward, in the direction of the base, when the clamping screw tips are forced into the holes, whereupon the cutting knife is pressed against the two clamping jaws and against the height-adjustable knife rest.

In the region between the two clamping jaws, the clamping plate has a tapered lead-off section contiguous with the knife to form a virtually projection-free plane so that the cut samples can slide off evenly.

BRIEF DESCRIPTION OF THE DRAWINGS

These and other features, aspects, and advantages of the present invention will become much more apparent from the following description, appended claims, and accompanying drawings where:

FIG. 1 shows a perspective view of the knife holder with direct gripping of the cutting knife in the clamping jaw.

FIG. 2 shows a perspective view of the additional clamping plate.

DETAILED DESCRIPTION OF THE PREFERRED EMBODIMENTS

Figure 3:
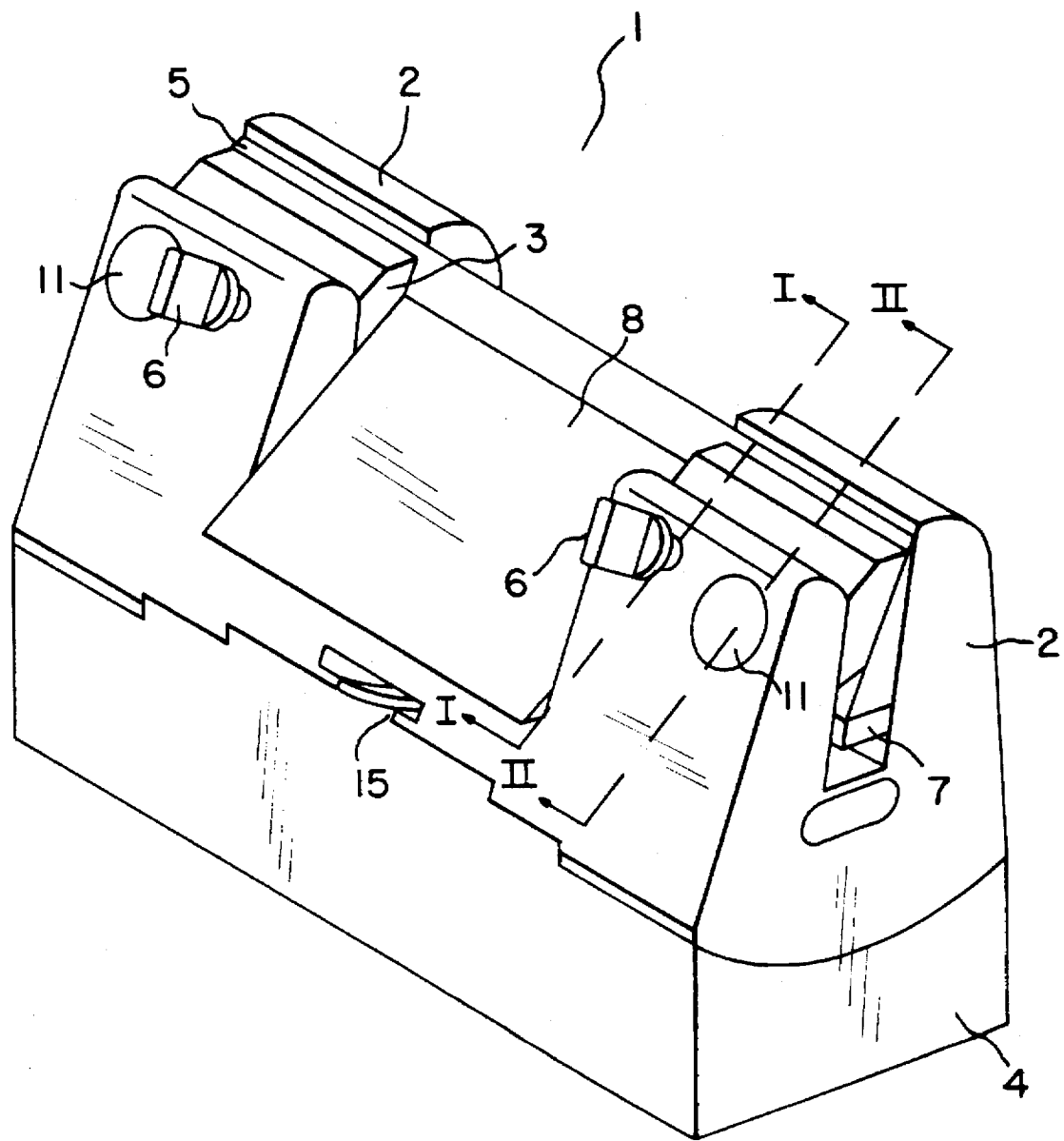
FIG. 3 shows a perspective view of the knife holder with gripping of the cutting knife via the clamping plate.

FIG. 1 shows a knife holder 1 with two clamping jaws 2 and a knife 5 clamped therebetween. The knife holder 1 is mounted pivotably on a base 4 for knife clearance angle adjustment, the lock 15 fixing the respectively adjusted clearance angle. Two clamping screws 6, in the upwardly open clamping jaws 2, act directly on the knife 5 so that it can be screwed in firmly by tightening the clamping screws 6. The cutting knife 5 lies with its knife-back narrow surface, opposite the knife blade edge, in a height-adjustable knife rest 7 integrated in the knife holder 1. Two covers 11 in the clamping jaws 2 serve to protect retrofittable suspensions 9 for a one-piece clamping plate 3.

FIG. 2 shows the one-piece clamping plate 3 with two side parts 16 for reception in the clamping jaws 2 and a wedge-shaped center part 8 for bearing against the blade region of the knife 5. Each of the side parts 16 has bores or holes 13 and 14. The clamping screws 6 for fixing the cutting knife 5 engage in the holes 13 while the holes 14 are provided with a thread and serve to connect the spring suspension of the clamping plate in the knife holder 1.

FIG. 3 shows the knife holder 1 with the knife 5 inserted and also integrated with the clamping plate 3. With this embodiment, increased stability in the blade region of the knife 5 is achieved. From this figure, it is also clear that the tapering center part 8 of the clamping plate 3 fits exactly to the knife rear surface of the cutting knife 5 so that, in spite of the clamping plate 3 bearing against the knife, a perfect sliding off of the cut object is possible.

Figure 4:
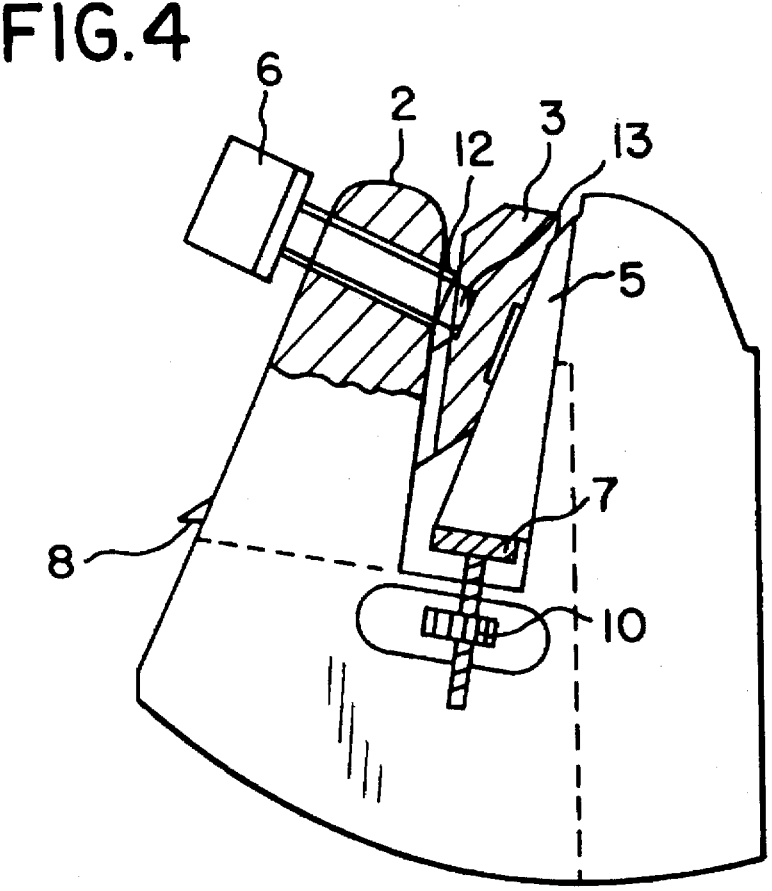
FIG. 4 is a cross-sectional view taken along the line I—I of FIG. 3.

FIG. 4 shows a cross-section taken along the line I—I of FIG. 3. The clamping screw 6 is guided via a thread through the clamping jaw 2 and has a conically shaped tip 12. This tip 12 engages in the bore 13 of the clamping plate 3 and presses the clamping plate 3 against the knife 5. In the unlocked state, the bore 13 of the clamping plate 3 lies raised in the direction of the knife blade in relation to the axis of the clamping screw 6. This has the consequence that, when the clamping screw 6 is screwed in, the conically shaped screw tip 12 first acts on the edge of the bore 13 and, on further screwing, presses the spring-mounted clamping plate 3 downward in the direction of the knife support 7. The wedge shape of the clamping plate 3, which is adapted to the cutting knife 5, simultaneously presses against the knife 5 and the knife support 7. The knife support 7 is arranged adjustably in the knife holder 1 via a height-adjustment device 10. This purpose is served by the diagrammatically indicated threaded rod and the adjusting screw.

Figure 5:
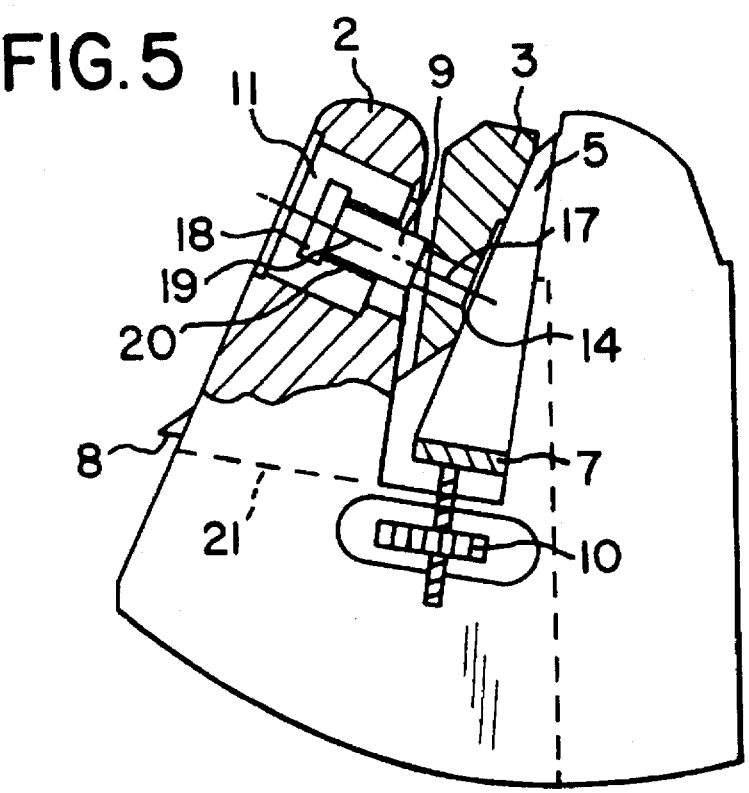
FIG. 5 is a cross-sectional view taken along the line II—II of FIG. 3.

FIG. 5 shows a cross-section taken along the line II—II of FIG. 3 with the spring suspension 9 for the clamping plate 3. The suspension 9, which has a screw 17 with a flat head 18 and a neck 19, is situated in the clamping jaw 2 behind the cover 11. The screw 17 engages in the threaded bore 14 of the clamping plate 3. The neck 19 is supported in this connection on the clamping jaw 2. A pressure spring 20, which is tensioned between the screw head 18 and the clamping jaw 2, is pushed via the screw 17.

The clamping plate 3 with the center part 8, which is supported by this spring suspension 9, is not supported on the bottom (line 21) between the clamping jaws 2, but is rather suspended or mounted freely. It is thus possible for the clamping plate 3, on tightening the clamping screws 6, to also adapt to the most different type of knife geometries and at the same time, on knife exchange, a free space or gap remains between the clamping plate 3 and the clamping jaw 2 for insertion of the knife 5.

The present invention makes it possible for a simply equipped knife holder for wedge-shaped cutting knives 5 to be changed over to a knife holder with increased stability in the knife blade region by inserting the one-piece clamping plate 3. In this connection, it is advantageous for the clamping jaws of the knife holder to be designed in an upwardly open manner. This enables a knife exchange to be carried out rapidly and safely. As a result of the spring suspension 9 of the clamping plate, a gap remains free between the clamping plate and the clamping jaw. The clamping plate is, in this connection, not supported on the bottom of the knife holder but is rather freely movable via the holding device. As a result, it is advantageously possible for the clamping plate to be adapted exactly to the different knife geometries and a safe gripping of the knife consequently takes place.

The bores in the clamping plate are arranged vertically or angularly offset in relation to the axis of the conically tapering clamping screws. This advantageously has the effect of the clamping plate being drawn downward in the direction of the base on screwing the clamping screws into the bore. As a result of the wedge shape between the clamping plate and the knife, the knife is pressed not only against the clamping jaw but also against the height-adjustable knife rest. As a result, a considerably increased stability of the knife in the blade region is achieved.

The tapering wedge shape of the clamping plate in the knife blade region fits exactly to the knife rear surface of the cutting knife and thus forms a virtually projection-free plane. The cut samples can slide off evenly on this plane.

Given the disclosure of the present invention, one versed in the art would appreciate the fact that there may be other embodiments and modifications within the scope and spirit of the present invention. Accordingly, all expedient modifications attainable by one versed in the art from the present disclosure within the scope and spirit of the present invention are to be included as further embodiments of the present invention. The scope of the present invention accordingly is to be defined as set forth in the appended claims.

I claim:

1. A knife holder for receiving a wedge-shaped knife comprising:
   a knife clamping device having a pair of laterally spaced clamping jaws, each of the clamping jaws having first and second opposingly spaced apart walls forming an upwardly open slot;
   a clamping screw secured to each of the clamping jaws and having a tip which is extendable through the first wall of the associated clamping jaw;
   a height-adjustable knife rest extending in the slots of the clamping jaws for supporting the knife;
   a clamping plate positioned in the slots between the first and second opposing walls thereof, whereby the knife is positionable in the slots between the clamping plate and the second walls of the clamping jaws, whereby the clamping screws push the clamping plate against the knife so that the knife rests against the second walls of the clamping jaws; and
   a spring suspension secured to each of the clamping jaws and the clamping plate to suspend the clamping plate between the first and second walls of the clamping jaws.

2. A knife holder according to claim 1, wherein the spring suspensions secured to the clamping jaws leave a gap between the clamping plate and the second walls of the clamping jaws to allow unhindered insertion of the knife.

3. A knife holder according to claim 1, wherein the tip of each clamping screw is conical and abuts against the clamping plate.

4. A knife holder according to claim 3, wherein the clamping plate has a pair of holes each for receiving one of the conical tips.

5. A knife holder according to claim 4, wherein each of the clamping screws is threaded to one of the clamping jaws and each of the holes is vertically offset in relation to the clamping screw tip in a direction that forces the clamping plate downward as the clamping screw tips are forced into the holes, whereby the clamping plate presses the knife inserted in the slots against the second walls of the clamping jaws and against the height-adjustable knife rest.

6. A knife holder according to claim 1, wherein the clamping jaws are integrally formed in one-piece.

7. A knife holder according to claim 1, wherein the clamping plate is integrally formed in one-piece.

8. A knife holder according to claim 1, wherein the clamping plate has, in the region between the clamping jaws, a tapered lead-off section contiguous with the knife positioned in the holder to form a virtually projection free plane to enable cut samples to slide off evenly.

9. A knife holder according to claim 8, wherein the height adjustable knife rest support a back end of the knife, opposite a cutting edge thereof.

10. A knife holder according to claim 1, wherein the knife holder is adapted for holding a regrindable hard metal or steel microtome knife.

11. A knife holder for receiving a wedge-shaped regrindable hard metal or steel knife comprising:

a base;

a pair of laterally spaced clamping jaws for receiving the knife, wherein the clamping jaws are mounted pivotally to the base to allow clearance angle adjustment of the knife, each of the clamping jaws having first and second opposingly spaced apart walls forming an upwardly open slot;

a clamping screw secured to each of the clamping jaws and having a tip which is extendable through the first wall of the associated clamping jaw;

a height-adjustable knife rest extending in the slots of the clamping jaws for supporting the knife;

a clamping plate positioned in the slots between the first and second opposing walls thereof, whereby the knife is positionable in the slots between the clamping plate and the second walls of the clamping jaws, whereby the clamping screws push the clamping plate against the knife so that the knife rests against the second walls of the clamping jaws; and a spring suspension secured to each of the clamping jaws and the clamping plate to suspend the clamping plate between the first and second walls of the clamping jaws.

12. A knife holder according to claim 11, wherein the spring suspension secured to the clamping plate leaves a gap between the clamping plate and the second walls of the clamping jaws to allow unhindered insertion of the knife.

13. A knife holder according to claim 11, wherein the tip of each clamping screw is conical and abuts against the clamping plate.

14. A knife holder according to claim 13, wherein the clamping plate has a pair of holes each for receiving one of the conical tips.

15. A knife holder according to claim 14, wherein each of the clamping screws is threaded to one of the clamping jaws and each of the holes is vertically offset in relation to the clamping screw tip in a direction that forces the clamping plate toward the base as the clamping screw tips are forced into the holes, whereby the clamping plate presses the knife inserted in the slots against the second walls of the clamping jaws and against the height-adjustable knife rest.

16. A knife holder assembly comprising:

a wedge-shaped microtome knife;

a base;

a pair of laterally spaced clamping jaws receiving the knife, wherein the clamping jaws are mounted pivotally to the base to allow clearance angle adjustment of the knife, each of the clamping jaws having first and second opposingly spaced apart walls forming an upwardly open slot;

a clamping screw secured to each of the clamping jaws and having a tip which is extendable through the first wall of the associated clamping jaw;

a height-adjustable knife rest extending in the slots of the clamping jaws, supporting the knife;

a clamping plate positioned in the slots between the first and second opposing walls thereof, wherein the knife is positioned in the slots, sandwiched between the clamping plate and the second walls of the clamping jaws, wherein the clamping screws push the clamping plate against the knife so that the knife rests against the second walls of the clamping jaws; and a spring suspension secured to each of the clamping jaws and the clamping plate to suspend the clamping plate between the first and second walls of the clamping jaws.

17. A knife holder assembly according to claim 21, wherein the spring suspensions suspend the clamping plate and leave a gap between the clamping plate and the second walls of the clamping jaws to allow unhindered insertion of the knife.

18. A knife holder assembly according to claim 21, wherein the tip of each clamping screw is conical and abuts against the clamping plate.

19. A knife holder assembly according to claim 18, wherein the clamping plate has a pair of holes each receiving one of the conical tips.

20. A knife holder assembly according to claim 19, wherein each of the clamping screws is threaded to one of the clamping jaws and each of the holes is vertically offset in relation to the clamping screw tip in a direction that forces the clamping plate toward the base as the clamping screw tips are forced into the holes, whereupon the clamping plate presses the knife inserted in the slots against the second walls of the clamping jaws and against the height-adjustable knife rest.

* * * * *